United States Patent
Somasundaram et al.

(10) Patent No.: US 10,492,892 B2
(45) Date of Patent: Dec. 3, 2019

(54) AUTOMATIC ALIGNMENT AND ORIENTATION OF DIGITAL 3D DENTAL ARCH PAIRS

(71) Applicant: 3M INNOVATIVE PROPERTIES COMPANY, St. Paul, MN (US)

(72) Inventors: Guruprasad Somasundaram, St. Paul, MN (US); Benjamin D. Zimmer, Maplewood, MN (US); Alexandra R. Cunliffe, St. Paul, MN (US); Mojtaba K. Elyaderani, Minneapolis, MN (US); Arash Sangari, Woodbury, MN (US); Evan J. Ribnick, St. Louis Park, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 15/597,479

(22) Filed: May 17, 2017

(65) Prior Publication Data

US 2018/0333231 A1    Nov. 22, 2018

(51) Int. Cl.
*A61C 9/00* (2006.01)
*G06T 19/20* (2011.01)

(52) U.S. Cl.
CPC .............. *A61C 9/004* (2013.01); *G06T 19/20* (2013.01); *G06T 2210/41* (2013.01)

(58) Field of Classification Search
CPC ...... A61C 9/004; G06T 19/20; G06T 2210/41
USPC ....................................................... 345/419
See application file for complete search history.

(56) References Cited

U.S. PATENT DOCUMENTS

| | | | |
|---|---|---|---|
| 7,027,642 B2 * | 4/2006 | Rubbert | A61C 7/00 382/154 |
| 7,068,825 B2 * | 6/2006 | Rubbert | A61C 7/00 382/128 |
| 7,077,647 B2 | 7/2006 | Choi et al. | |
| 7,442,041 B2 | 10/2008 | Imgrund et al. | |
| 7,471,821 B2 | 12/2008 | Rubbert et al. | |
| 7,605,817 B2 | 10/2009 | Zhang et al. | |
| 7,695,278 B2 | 4/2010 | Sporbert et al. | |
| 7,826,646 B2 | 11/2010 | Pavlovskaia et al. | |

(Continued)

OTHER PUBLICATIONS

"Principal Component Analysis," retrieved from the internet on Jul. 12, 2017, URL <http://en.wkipedia.org/wiki/Principal_component_analysis>, 2017, pp. 1-15.

(Continued)

*Primary Examiner* — Hai Tao Sun

(57) ABSTRACT

A method for aligning digital 3D models of dental arch pairs, including a mandible and maxilla, to bring them into bite alignment. The method estimates representative planes for the mandible and maxilla 3D models and transforms the models such that the representative planes are each aligned with their respective coordinate systems and shown in a horizontal view. The method also transforms the models such that the mandible and maxilla are each aligned with a same coordinate system and shown in a front view. The digital 3D models are then brought into bite alignment such that the mandible is in occlusion with the maxilla or within a distance near to occlusion. The digital models of the bite-aligned arch pairs can also be transformed or rotated to be shown centered in a front view.

18 Claims, 5 Drawing Sheets

(56) References Cited

U.S. PATENT DOCUMENTS

| | | |
|---|---|---|
| 7,956,862 B2 | 6/2011 | Zhang et al. |
| 8,075,306 B2 | 12/2011 | Kitching et al. |
| 8,244,028 B2 | 8/2012 | Kuo et al. |
| 8,275,180 B2 | 9/2012 | Kuo |
| 2005/0271996 A1* | 12/2005 | Sporbert ............ A61C 7/00 433/24 |
| 2009/0316966 A1* | 12/2009 | Marshall ........... A61B 6/5217 382/128 |
| 2012/0015316 A1* | 1/2012 | Sachdeva ........... G06T 17/00 433/24 |
| 2015/0111177 A1* | 4/2015 | Fisker ............... A61C 13/01 433/196 |
| 2016/0070821 A1 | 3/2016 | Somasundaram et al. |
| 2018/0008384 A1* | 1/2018 | Schulter ............. A61K 6/0017 |

OTHER PUBLICATIONS

Roweis, "Nonlinear Dimensionality Reduction by Locally Linear Embedding," Science, 2000, vol. 290, pp. 2323-2326.

* cited by examiner

AUTOMATIC ALIGNMENT AND ORIENTATION OF DIGITAL 3D DENTAL ARCH PAIRS

BACKGROUND

The use of intra-oral three-dimensional (3D) scanners is becoming increasingly widespread. These scanners produce digital 3D models which represent the 3D structure of a patient's dentition, including both hard and relevant soft tissues. These 3D scans are useful in many applications, most commonly for digital dental and orthodontic workflows such as in the creation of crowns, implants, and appliances. Using these intra-oral scanners, it is possible to acquire 3D scans of both the maxillary and mandibular arches. In general, the digital 3D representations of the arches may not be placed in an orientation with respect to the desired viewpoint or even with respect to one another. Accordingly, a need exists to automatically detect and adjust those orientations of digital 3D dental arch pairs.

SUMMARY

A method for aligning dental arch pairs, consistent with the present invention, includes receiving a first digital 3D model of at least a portion of a person's mandible and a second a digital 3D model of at least a portion of the person's maxilla. First and second representative planes are estimated for the mandible and maxilla. The first and second digital 3D models are transformed such that the first and second representative planes are each aligned with their respective coordinate systems. The first and second digital 3D models are also transformed such that the mandible and the maxilla are each aligned with the same coordinate system. The first digital 3D model is brought into bite alignment with the second digital 3D model, after the transformations, such that the mandible is bite-aligned with the maxilla. The bite-aligned digital 3D models can also be transformed or rotated such that the mandible and maxilla are shown in a front view.

BRIEF DESCRIPTION OF THE DRAWINGS

The accompanying drawings are incorporated in and constitute a part of this specification and, together with the description, explain the advantages and principles of the invention. In the drawings.

DETAILED DESCRIPTION

Described herein are techniques for automatically aligning and orienting a pair of 3D dental arches, such as the mandible and maxilla scans (a person's upper and lower arches). The technique can result in arch pairs that are oriented so they point in a standard direction and are close to one another and mutually oriented in bite alignment shown in a horizontal front view. The techniques can also align and orient arch pairs in other directions and views.

Figure 1:
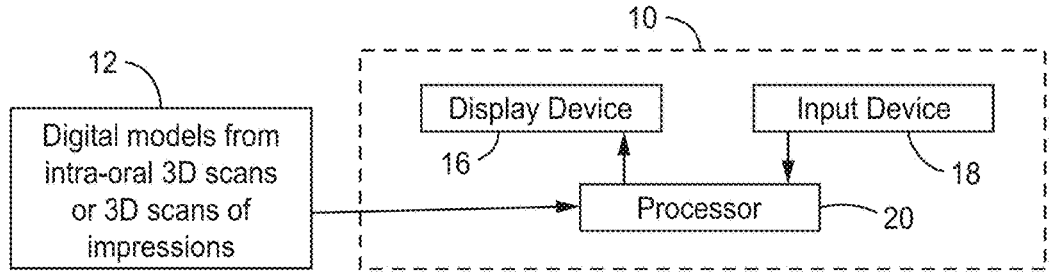
FIG. 1 is a diagram of a system for receiving and processing digital 3D models based upon intra-oral 3D scans or 3D scans from impressions.

FIG. 1 is a diagram of a system 10 for receiving and processing digital 3D models based upon intra-oral 3D scans. System 10 includes a processor 20 receiving digital 3D models of teeth (12) from intra-oral 3D scans or scans of impressions of teeth. System 10 can also include an electronic display device 16, such as a liquid crystal display (LCD) device, and an input device 18 for receiving user commands or other information. Systems to generate digital 3D images or models based upon image sets from multiple views are disclosed in U.S. Pat. Nos. 7,956,862 and 7,605,817, both of which are incorporated herein by reference as if fully set forth. These systems can use an intra-oral scanner to obtain digital images from multiple views of teeth or other intra-oral structures, and those digital images are processed to generate a digital 3D model representing the scanned teeth. System 10 can be implemented with, for example, a desktop, notebook, or tablet computer. System 10 can receive the 3D scans locally or remotely via a network.

The 3D scans addressed herein are represented as triangular meshes. The triangular mesh is common representation of 3D surfaces and has two components. The first component, referred to as the vertices of the mesh, are simply the coordinates of the 3D points that have been reconstructed on the surface—i.e., a point cloud. The second component, the mesh faces, encodes the connections between points on the object and is an efficient way of interpolating between the discrete sample points on the continuous surface. Each face is a triangle defined by three vertices, resulting in a surface that can be represented as a set of small triangular planar patches.

The techniques described herein use 3D scans of a patient's mandible and maxilla that have already been acquired. In some cases, these scans are full-arch, meaning they include all the teeth in the arch; in other cases, they can be quadrant scans which include only 4-6 teeth. Likewise, in some cases the scans of the two arches can be bite-aligned, meaning that the arches are positioned relative to one another in 3D space such that the teeth are in occlusion. However, in general the arches can be positioned in any arbitrary 3D position with respect to one another. In either case, the technique estimates 3D transformations, including rigid-body rotations and translations, that move the arches into positions in 3D space such that the following can occur: the arches are bite-aligned with one another so that the teeth are in at least approximate occlusion; the bite plane is horizontal, parallel to the X-Z plane; the arches are oriented in a standard direction, facing along the Z-axis; and the arches are centered about the origin.

The coordinate system used herein is for illustrative purposes only, and the described techniques can be used to align and orient arch pairs among other coordinate systems and in other views. For example, a bite-aligned arch pair can be shown in a side view, where the front of the bite-aligned arch pair faces the X-axis and a side of the pair faces the Z-axis from a viewer's perspective. Also, once the arch pair is bite-aligned, a viewer can optionally interact with the bite-aligned arch pair by rotating it to see a desired view.

Figure 2:
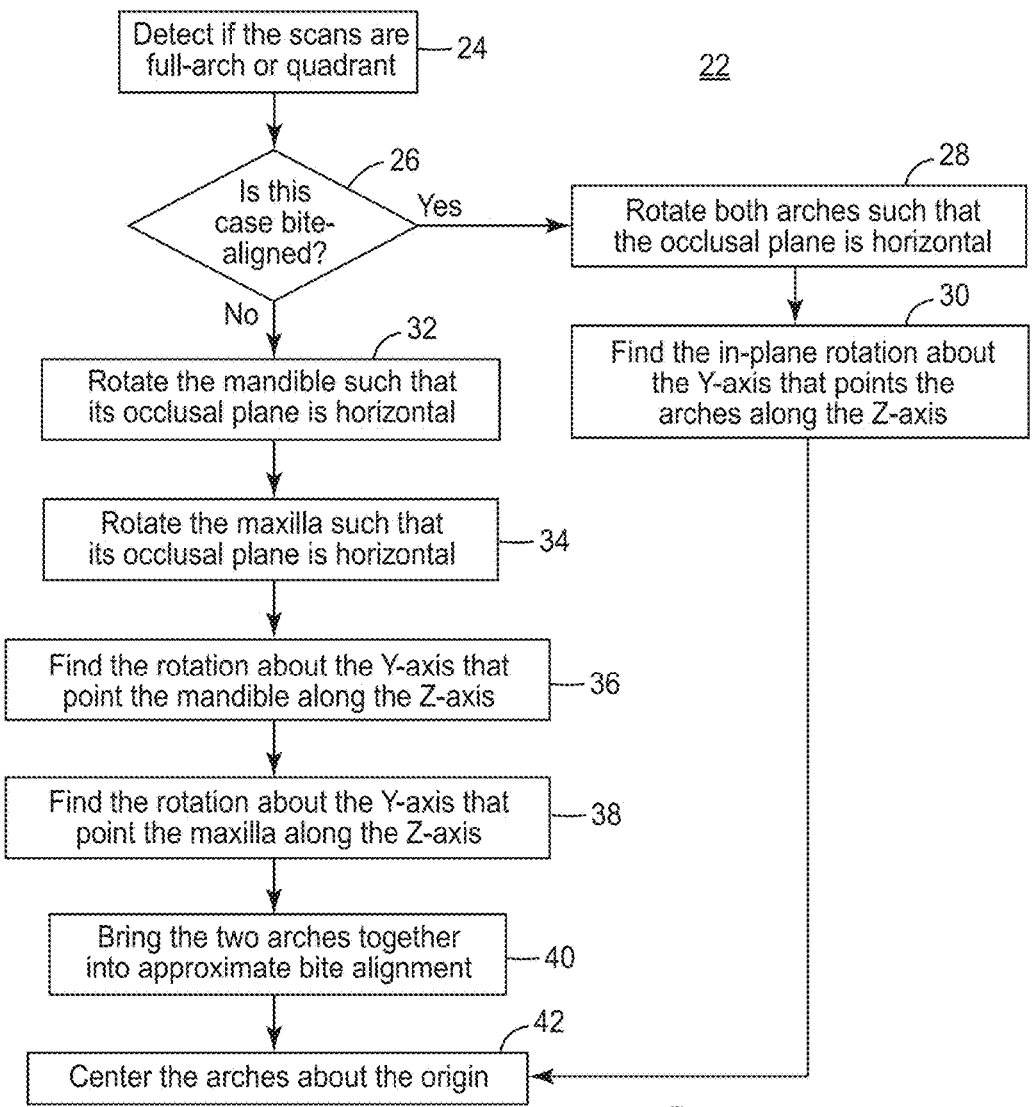
FIG. 2 is a flow chart of a method for automatic alignment and orientation of dental arch pairs.

In order to accomplish these alignment and orientation techniques, method 22 in the flow chart of FIG. 2 can be used to process a received case that includes digital 3D scans of a mandibular arch and a maxillary arch from the same person. Method 22 can be implemented in software or firmware modules, for example, for execution by processor 20, and can alternatively be implemented in hardware modules or a combination of software and hardware.

Method 22 includes detecting if the scans, for example received scans 12, are full-arch or quadrant (step 24) and determining if the scans are bite-aligned (step 26). If the scans are already bite-aligned, then method 22 includes transforming (e.g., rotating) both arches such that the representative plane (e.g., occlusal plane) is horizontal (step 28), finding the in-plane rotation about the Y-axis that points the arches along the Z-axis (step 30), and centering the arches about the origin (step 42).

If the scans are not bite-aligned (step 26), then method 22 includes the following: transforming (e.g., rotating) the mandible such that its representative plane (e.g., occlusal plane) is horizontal (step 32); transforming (e.g., rotating) the maxilla such that its representative plane (e.g., occlusal plane) is horizontal (step 34); finding the transformation (e.g., rotation) about the Y-axis that points the mandible along the Z-axis (step 36); finding the transformation (e.g., rotation) about the Y-axis that points the maxilla along the Z-axis (step 38); bringing the two arches together into at least approximate bite alignment (step 40); and centering the arches about the origin (step 42).

Transforming (and transformation) may include but is not limited to a rotation or a translation or a combination of both rotation and translation.

Each of these steps is described below, along with other processing steps included within them. As also explained below, steps 30, 36, and 38 are different depending upon whether the scans are full-arch or quadrant.

Several of the steps in method 22 require an arch curve parameterization, essentially a smooth one-dimensional (1D) curve that traverses the arch and follows the tops of the teeth.

Figure 3:
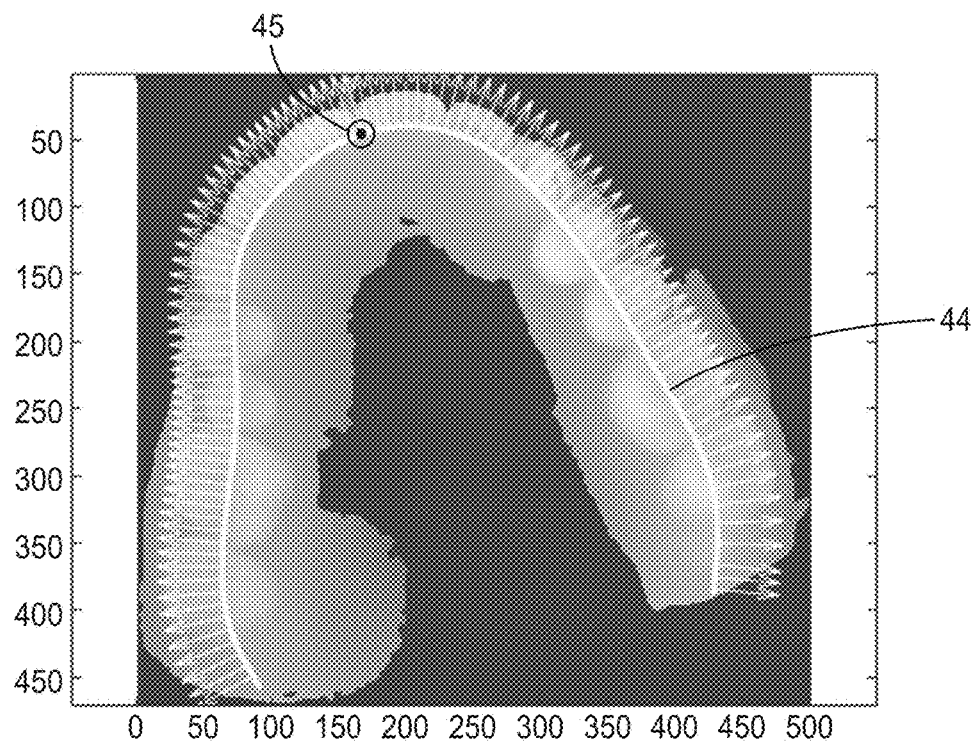
FIG. 3 is an example of an arch-curve parameterization.

This curve can be determined by computing a 1D manifold embedding of the upper parts of the scans (i.e., the parts nearer to the occlusal surface) using techniques such as Locally Linear Embedding (LLE). An example of an arch curve parameterization is shown in FIG. 3 with a 1D curve 44 overlaid on an image of an arch. The arrows emanating from the arch indicate its normal direction.

Figure 4:
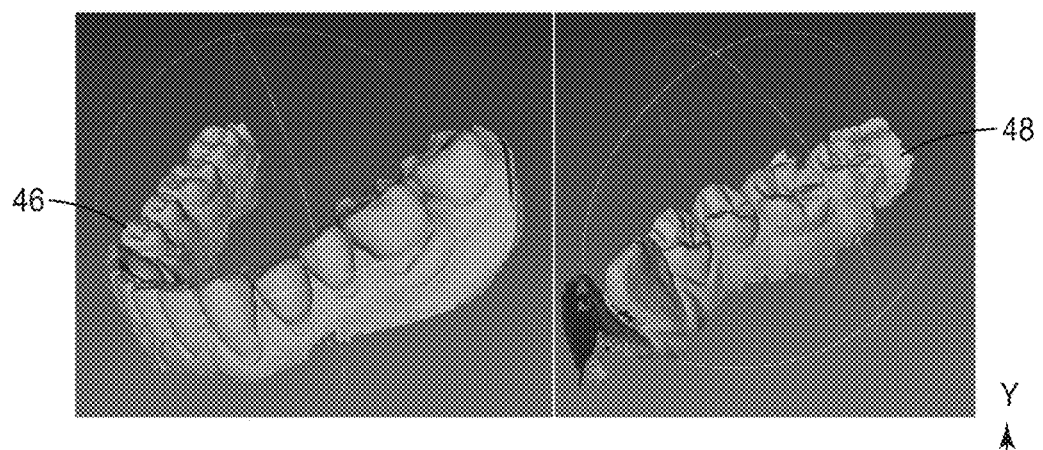
FIG. 4 is an example of a full arch-scan and a quadrant scan.

The acquired 3D models can be either full-arch scans, covering all the teeth present in an arch, or quadrant scans, covering only 4-6 teeth. Examples of both types of scans are shown in FIG. 4, illustrating a full-arch scan 46 and a quadrant scan 48.

Whether a scan is full-arch or quadrant can be determined automatically by parameterizing the arch, as illustrated in FIG. 3, and measuring the geodesic length of the curve, for example curve 44. Full-arch scans will result in longer arch curves than quadrant scans, and a suitable length threshold will differentiate between the two. In practice, a suitable threshold may be, for example, 70 mm, where arch curves greater than the threshold are deemed a full-arch and arch curves equal to or less than the threshold are deemed a quadrant. Other thresholds can also be used.

For embodiments of this invention, a pair of arch scans (i.e., mandibular and maxillary arches) are considered to be in bite alignment if they are close together in the directions normal (perpendicular) to their representative planes, and there is significant overlap between them when projected onto their representative planes. Being close together for bite alignment provides for the arch pairs being in occlusion, meaning in contact with one another, or within a particular distance from occlusion such as within 20 mm, meaning the bite-aligned arch pairs are 20 mm or less apart.

Representative planes can be estimated using various techniques, for example the techniques described in the section entitled "Alignment Method 3—Regression or Plane Fitting" in US Patent Application Publication No. 2016/0070821, and specifically in Table 3 therein. The Support Vector Regression (SVR) approach has been found to robustly estimate the representative plane for a single arch, regardless of whether it is a quadrant of full-arch scan. Table 1 provides exemplary pseudocode for implementing this SVR approach to estimate representative planes.

TABLE 1

Input: a 3D mesh with a set of vertices V specified in 3D coordinate system X, Y and Z. Y represents the rough direction of vertical axis in which the teeth point upwards.
Output: the normal vector perpendicular to representative plane which represents the desired upward direction of teeth.
Assumptions: Teeth are roughly pointing up along the Y axis. The mesh has been truncated below the gum line.

Method steps:

1  Subtract the mean of data points to centralize the data points around (0, 0, 0).
2  Apply the SVR with linear kernel and margin value ε to find the representative plane.
3  Find the normal direction of the representative plane by geometrical methods or applying a simple PCA.

The result of this representative plane estimation is a plane of the form:

$$ax+by+cz+d=0$$

where the plane normal vector is given by:

$$n=[a\ b\ c]^T$$

Figure 5:
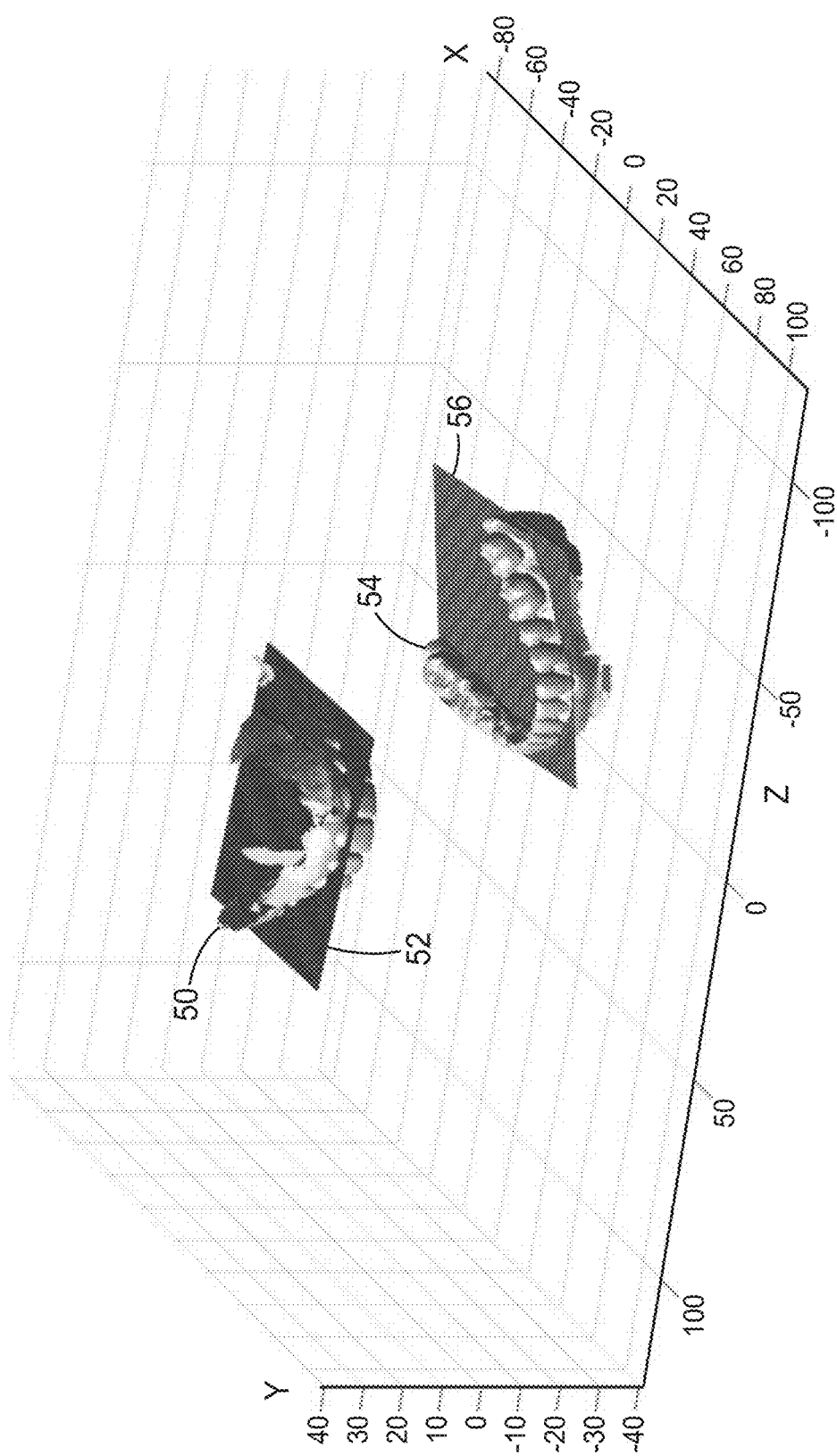
FIG. 5 is an example of an arch pair that is not bite-aligned along with the estimated representative planes.
Figure 6:
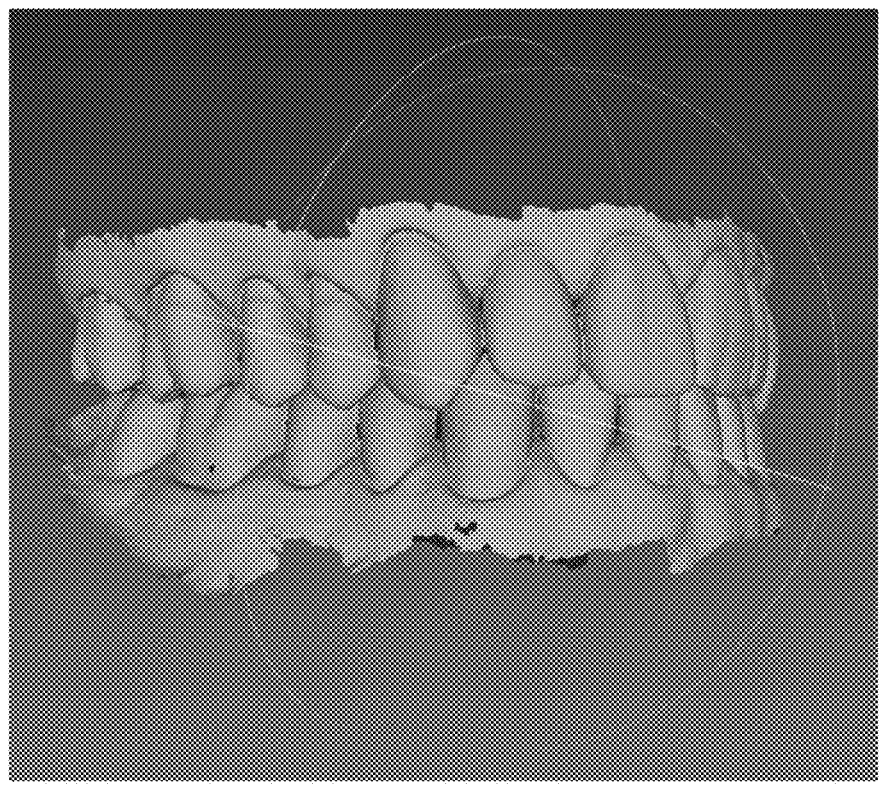
FIG. 6 is an example of an arch pair that is bite-aligned.

FIG. 5 shows an example of a pair of arches 50 and 54, which are not bite-aligned, along with their estimated representative planes 52 and 56, respectively. An example of an arch pair that is bite-aligned is shown in FIG. 6. In addition to being bit-aligned, the arch pair shown in FIG. 6 is also oriented for a desired view, in this case a front view where the arches are facing the Z-axis from a viewer's perspective and are essentially horizontal with respect to the X-Z plane.

As mentioned above, one criteria for deciding whether two arches are bite-aligned is based on the distances between the two representative planes of the arches in their normal directions. This can be computed according to the method in Table 2 (steps 2a, 2b, and 2c) for the mandibular arch.

TABLE 2

Assuming that the mandible representative plane is given by $n_{man}^T x + d_{man}$, and the maxilla representative plane is given by $n_{max}^T x + d_{max}$, perform the method steps:

2a  Compute the centroid of the mandible in (x, y, z), which is simply the mean of the 3D coordinates of all of its mesh vertices. This point is denoted as $x_c = [x_c\ y_c\ z_c]^T$.

TABLE 2-continued

2b  Compute the point on the mandible representative plane that is closest to the mandible centroid $x_c$. This point is given by:
$$\hat{x}_c = x_c + \lambda n_{man}$$
where:
$$\lambda = -\frac{1}{n_{man}^T n_{man}}(n_{man}^T x_c + d_{man})$$

2c  Compute the distance from the point $\hat{x}_c$, on the mandible representative plane, to the maxilla representative plane, according to:
$$d = \frac{1}{\|n_{max}\|}|n_{max}^T \hat{x}_c + d_{max}|$$

The method in Table 2 is repeated for the maxillary arch. If these distances are large, this indicates that the mandible and maxilla representative planes are far apart, as illustrated in FIG. 5.

A second criteria for determining whether two arches are in bite alignment is based on how much overlap there is between the two arches when projected onto a plane. This is accomplished by first projecting both arches onto the representative plane of the smaller arch, and then measuring how much of the area occupied by one arch is occupied by the other arch in this two-dimensional (2D) projection. If the representative plane of the smaller arch is given by n and d, then a coordinate system is formed in which the Y-axis is a normal vector and the X- and Z-axes are orthogonal, and the vertices from both meshes are projected onto the X- and Z-axes, resulting in 2D coordinate for each point. This 2D space is quantized, and percentage of overlapping cells (occupied by both arches) is tabulated.

As identified above and described in Table 1, one of the techniques described in US Patent Application Publication No. 2016/0070821 can be used to fit an approximate representative plane to each arch. An example of this is shown in FIG. 5. The goal, then, is to rotate the arch in 3D space such that this representative plane becomes horizontal, meaning parallel to the X-Z plane for the coordinate system used herein.

The procedure for computing this rotation is as follows. If the plane for an arch is given by $n^T x + d = 0$, a goal is to compute a new coordinate system in which this plane is horizontal. This new basis can be represented as $[a_1\ a_2\ a_3]$, where:
1. The new Y-axis $a_2 = n/\|n\|$, so that it is parallel to a normal vector of the plane. For consistency, the procedure also ensures that the dot product of $a_2$ and the original the origin Y-axis $[0\ 1\ 0]^T$ is positive, and negating $a_2$ if it is not.
2. The new X-axis is chosen to be orthogonal to both the prior Z-axis, and the new Y-axis, according to $a_1 = a_2 \times [0\ 0\ 1]^T$. As before, for consistency, the procedure ensures that the dot product of $a_1$ and the original X-axis is positive, and negate $a_1$ if it is not.
3. Finally, the new Z-axis is chosen to be orthogonal to the new X- and Y-axes: $a_3 = a_1 \times a_2$, again ensuring that this has a positive dot product with the original Z-axis.

The rotation matrix can then be formed $R = [a_1\ a_2\ a_3]$, and each vertex is rotated in 3D according to $x' = Rx$.

When the scans have been found to be already bite-aligned, then both arches are rotated according to the representative plane of the mandibular arch. Otherwise, when the scans are not bite-aligned, each arch is rotated separately according to its own representative plane.

After ensuring that the representative planes are horizontal, the arches are rotated in-plane, about the Y-axis, so they are aligned in a standard orientation along the Z-axis. This rotation is estimated differently based on whether the scan is a full-arch or a quadrant scans, described below. In cases where the scans are not bite-aligned, this rotation about the Y-axis is estimated independently for each arch. Otherwise, when the scans are bite-aligned, the mean of the rotations estimated for the two arches is used.

The arch curve parameterization described above results in a smooth 1D curve that traverses the arch, for example curve 44 illustrated in FIG. 3. Given this curve, its mid-point can be estimated by finding the point along the curve at which half of its geodesic distance is on either side, for example point 45 on curve 44 in FIG. 3.

The normal vector of the arch curve at the location of its mid-point is extracted. The orientation of this vector is given simply by the arctangent of its elements in the X- and Z-axes. Then, this angle gives the amount by which the arch should be rotated, about the Y-axis, in order that this mid-point will be facing directly along the Z-axis.

For quadrant scans a different approach is taken, since the arch mid-point is no longer a fixed location along the arch, but heavily dependent on which teeth are included in the scan. Instead, a goal in the case of a quadrant scan is to simply align the arch along the direction of the Z-axis as much as possible. This is accomplished by computing the first principal component of the vertices in 3D, using Principal Component Analysis (PCA), and then rotating the mesh so that this component is aligned with the Z-axis.

In cases where the arches are not bite-aligned, the arches are brought into approximate alignment as follows. First the maxilla is shifted along the Y-axis so that its representative plane is a desired distance from that of the mandibular plane, for example the planes should be in at least approximate occlusion by being 20 mm or less apart. Then, the maxilla is shifted in the X-Z plane such that its centroid is aligned with the centroid of the mandible.

Figure 7:
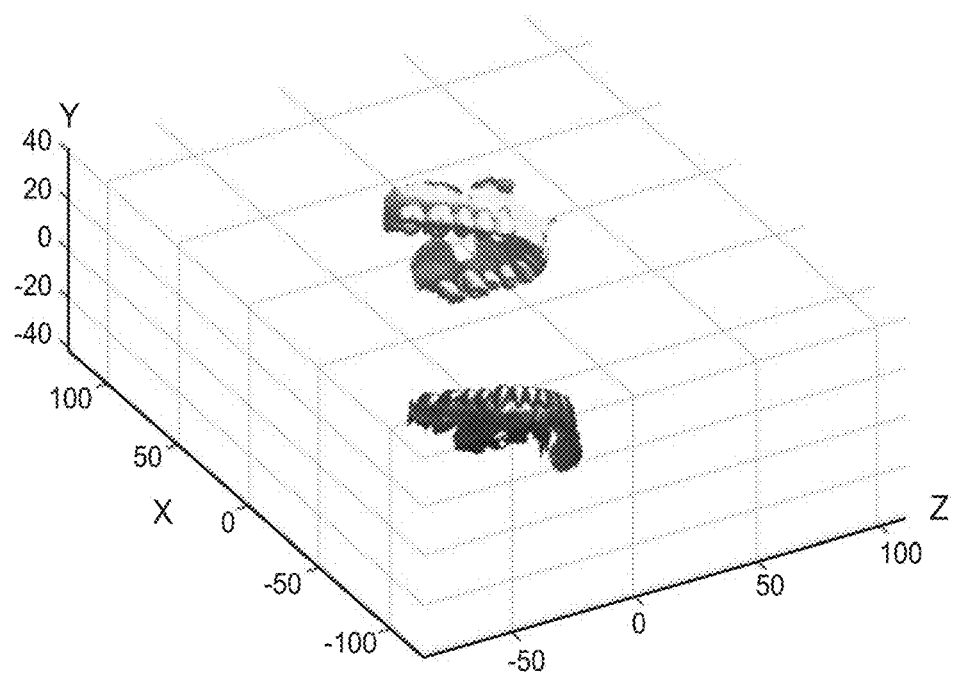
FIG. 7 is an example of an arch pair before being brought into bite alignment.
Figure 8:
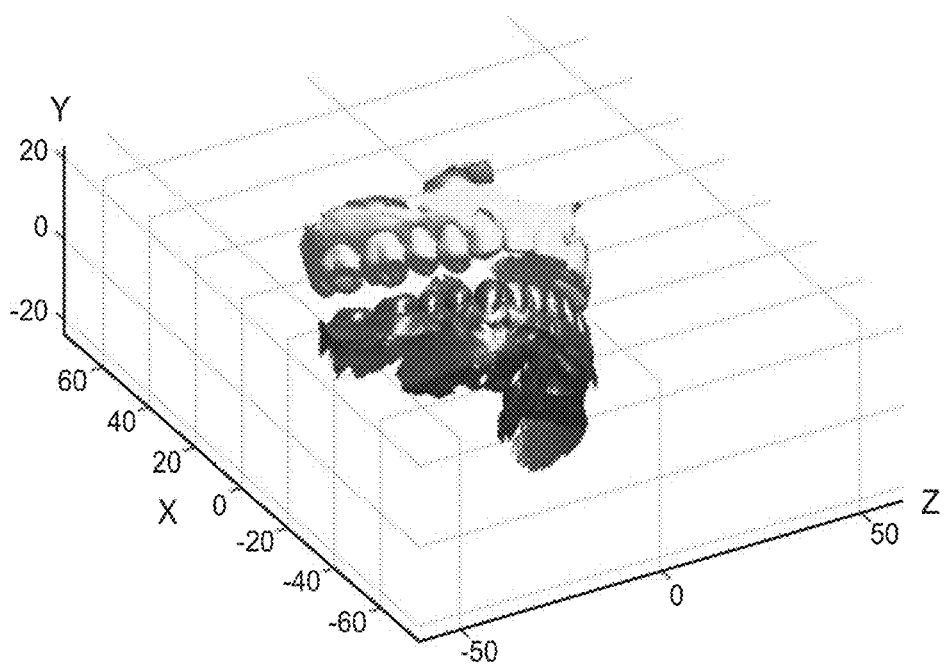
FIG. 8 illustrates the arch pair of FIG. 7 in approximate bite alignment.

An example of an arch pair before and after being brought into approximate bite alignment is shown in FIGS. 7 and 8, respectively.

Another embodiment includes the following process. Automated bite alignment of arch pair scans can be achieved through a combination of 3D mesh processing and optimization. First, upper and lower arches are roughly aligned in the up-down direction (to be essentially parallel with the Z-axis), defined as the principle component with the smallest corresponding eigenvalue when PCA is applied to the mesh vertices. The arches are subsequently oriented so they are aligned in the X-Y plane. This can be achieved either by aligning the 1D parameterized arch forms, or by identifying the location of the landmarks on the teeth such as canines and setting the landmarks so that they are aligned along the X-Y plane, for example tips of each pair of upper and lower canines so that the distance between each pair of canines is below a threshold value. Another approach to anatomical landmarks is to use geometric features (e.g., spin image descriptors) around each vertex of the mesh. Then, the vertices of lower arch and upper arch with similar spin image descriptors are matched with each other, and a robust rigid-body transformation that aligns most of the matched vertices is estimated and applied to the upper arch. Arches are subsequently transformed in 3D in an iterative manner until all directed distances are positive and minimized. For example, the 3D transformation can be determined using a constrained Iterative Closest Point (ICP) algorithm. This constrained/penalized ICP algorithm estimates a rigid-body transformation between two meshes where the negative directed distance between meshes is penalized more aggressively compared to the positive directed distance, or vice versa. This other embodiment can be used to present the bite-aligned arches with teeth in occlusion.

The invention claimed is:

1. A computer-implemented method for aligning dental arch pairs, comprising steps of executed by a processor:
   receiving a first digital 3D model of at least a portion of a person's mandible and a second a digital 3D model of at least a portion of the person's maxilla;
   automatically detecting whether the first digital 3D model represents a full-arch of the mandible;
   automatically detecting whether the first digital 3D model represents a quadrant arch of the mandible;
   automatically detecting whether the second digital 3D model represents a full-arch of the maxilla;
   automatically detecting whether the second digital 3D model represents a quadrant arch of the maxilla;
   estimating a first representative plane in the first digital 3D model for the mandible and a second representative plane in the second digital 3D model for the maxilla;
   first transforming the first digital 3D model and the second digital 3D model such that the first representative plane and the second representative plane are each aligned with respective coordinate systems;
   second transforming the first digital 3D model and the second digital 3D model such that the mandible and the maxilla in the digital 3D models are each aligned with a same coordinate system; and
   bringing the first digital 3D model into bite alignment with the second digital 3D model, after the transforming steps, such that the mandible is bite-aligned with the maxilla in the digital 3D models.

2. The method of claim 1, further comprising transforming the first and second digital 3D models such that the bite-aligned mandible and maxilla are oriented in a front view.

3. The method of claim 1, wherein the first transforming step comprises transforming the first and second digital 3D models such that the first and second representative planes are horizontal from a viewer's perspective.

4. The method of claim 1, wherein the second transforming step comprises transforming the first and second digital 3D models such that the mandible and maxilla in the digital 3D models are each oriented for a same particular view.

5. The method of claim 1, wherein the detecting steps comprise:
   overlaying a first curve on the first digital 3D model that traverses the mandible and determining whether the length of the first curve is greater than a threshold; and
   overlaying a second curve on the second digital 3D model that traverses the maxilla and determining whether the length of the second curve is greater than the threshold.

6. The method of claim 1, wherein the bringing step comprises:
   first shifting the first or second digital 3D model such that the second representative plane is a particular distance from the first representative plane; and
   second shifting the first or second digital 3D model such that a centroid of the mandible is aligned with a centroid of the maxilla in the digital 3D models.

7. The method of claim 6, wherein the first shifting step comprises shifting the second digital 3D model such the second representative plane is within 20 mm of the first representative plane.

8. The method of claim 1, wherein the bringing step comprises transforming the first and second digital 3D models in an iterative manner until directed distances between the mandible and the maxilla in the digital 3D models are positive and minimized.

9. A system for aligning dental arch pairs, comprising:
   a module for receiving a first digital 3D model of at least a portion of a person's mandible and a second a digital 3D model of at least a portion of the person's maxilla;
   a module for automatically detecting whether the first digital 3D model represents a full-arch of the mandible;
   a module for automatically detecting whether the first digital 3D model represents a quadrant arch of the mandible;
   a module for automatically detecting whether the second digital 3D model represents a full-arch of the maxilla;
   a module for automatically detecting whether the second digital 3D model represents a quadrant arch of the maxilla;
   a module for estimating a first representative plane in the first digital 3D model for the mandible and a second representative plane in the second digital 3D model for the maxilla;
   a module for first transforming the first digital 3D model and the second digital 3D model such that the first representative plane and the second representative plane are each aligned with respective coordinate systems;
   a module for second transforming the first digital 3D model and the second digital 3D model such that the mandible and the maxilla in the digital 3D models are each aligned with a same coordinate system; and
   a module for bringing the first digital 3D model into bite alignment with the second digital 3D model, after the transforming, such that the mandible is bite-aligned with the maxilla in the digital 3D models.

10. The system of claim 9, further comprising a module for transforming the first and second digital 3D models such that the bite-aligned mandible and maxilla are oriented in a front view.

11. The system of claim 9, wherein the first transforming module comprises a module for transforming the first and second digital 3D models such that the first and second representative planes are horizontal from a viewer's perspective.

12. The system of claim 9, wherein the second transforming module comprises a module for transforming the first and second digital 3D models such that the mandible and maxilla in the digital 3D models are each oriented for a same particular view.

13. The system of claim 9, wherein the detecting modules comprise:

a module for overlaying a first curve on the first digital 3D model that traverses the mandible and determining whether the length of the first curve is greater than a threshold; and a module for overlaying a second curve on the second digital 3D model that traverses the maxilla and determining whether the length of the second curve is greater than the threshold.

14. The system of claim 9, wherein the bringing module comprises:

a module for first shifting the first or second digital 3D model such that the second representative plane is a particular distance from the first representative plane; and a module for second shifting the first or second digital 3D model such that a centroid of the mandible is aligned with a centroid of the maxilla in the digital 3D models.

15. The system of claim 14, wherein the first shifting module comprises a module for shifting the second digital 3D model such the second representative plane is within 20 mm of the first representative plane.

16. The system of claim 9, wherein the bringing module comprises a module for transforming the first and second digital 3D models in an iterative manner until directed distances between the mandible and the maxilla in the digital 3D models are positive and minimized.

17. The method of claim 1, wherein the second transforming step comprises:

automatically rotating the first and second digital 3D models such that mid-points of the mandible and the maxilla are each aligned with the same coordinate system, if the first and second digital 3D models each represent full-arches; and automatically rotating the first and second digital 3D models such that principal components of the mandible and the maxilla are each aligned with the same coordinate system, if the first and second digital 3D models each represent quadrant arches.

18. The system of claim 9, wherein the second transforming module comprises:

a module for automatically rotating the first and second digital 3D models such that mid-points of the mandible and the maxilla are each aligned with the same coordinate system, if the first and second digital 3D models each represent full-arches; and a module for automatically rotating the first and second digital 3D models such that principal components of the mandible and the maxilla are each aligned with the same coordinate system, if the first and second digital 3D models each represent quadrant arches.

* * * * *